United States Patent
Peralta

(10) Patent No.: US 7,303,581 B2
(45) Date of Patent: Dec. 4, 2007

(54) ARTIFICIAL HEART USING MAGNETOHYDRODYNAMIC PROPULSIONH

(76) Inventor: Eduardo J. Peralta, 2295 Pavillion Dr., Santa Ana, CA (US) 92705

( * ) Notice: Subject to any disclaimer, the term of this patent is extended or adjusted under 35 U.S.C. 154(b) by 0 days.

(21) Appl. No.: 11/218,950

(22) Filed: Sep. 2, 2005

(65) Prior Publication Data

US 2006/0058873 A1 Mar. 16, 2006

Related U.S. Application Data

(60) Provisional application No. 60/609,164, filed on Sep. 10, 2004.

(51) Int. Cl.
*A61M 1/10* (2006.01)
(52) U.S. Cl. .................................................. 623/3.27
(58) Field of Classification Search ......... 623/3.1–3.28
See application file for complete search history.

(56) References Cited

U.S. PATENT DOCUMENTS

| | | | |
|---|---|---|---|
| 3,206,768 A * | 9/1965 | Preston | 623/3.28 |
| 3,568,214 A | 3/1971 | Goldschmied | |
| 3,633,217 A * | 1/1972 | Lance | 623/3.19 |
| 3,768,931 A | 10/1973 | Willis, Jr. | |
| 3,874,002 A | 4/1975 | Kurpanek | |
| 4,152,785 A | 5/1979 | Shumakov et al. | |
| 4,396,055 A | 8/1983 | Mitchell, Jr. | |
| 4,599,083 A | 7/1986 | Perlov et al. | |
| 4,621,617 A | 11/1986 | Sharma | |
| 4,650,485 A | 3/1987 | Della Sala | |
| 4,869,656 A | 9/1989 | Della Sala | |
| 5,685,698 A * | 11/1997 | Smoll | 417/50 |
| 6,074,365 A | 6/2000 | Hahndel et al. | |
| 6,123,724 A | 9/2000 | Denker | |
| 6,251,061 B1 | 6/2001 | Hastings et al. | |
| 6,342,071 B1 * | 1/2002 | Pless | 623/3.1 |
| 6,440,059 B1 * | 8/2002 | Haas et al. | 600/17 |
| 6,579,315 B1 * | 6/2003 | Weiss | 623/3.27 |

OTHER PUBLICATIONS

Hayt, Jr. William H. Engineering Electromagnetics. McGraw-Hill Book Co., Inc., 1958.

(Continued)

*Primary Examiner*—Bruce Snow
*Assistant Examiner*—Cheryl Miller
(74) *Attorney, Agent, or Firm*—Leonard Tachner

(57) ABSTRACT

An implantable artificial heart apparatus which has no moving parts. It employs the technology of magnetohydrodynamics (MHD) to induce flow of human blood. An MHD propulsion unit is a device which applies magnetic and electric fields to blood to propel the conductive fluid through the body's circulatory system. Electricity is passed through the blood via electrodes at the same junction where the blood is exposed to the magnetic field. Charged ions that move from anode to cathode create their own corresponding magnetic fields which are either attracted or repelled by the externally applied magnetic field. The result is propulsion in a uniform direction with the moving ions, in effect, dragging fluid molecules with them. A single MHD propulsion unit performs the combined functions of the atrium and the ventricle of the human heart. Two MHD propulsion units are required to perform the full cardiac cycle of the heart, one to pump unoxygenated blood through the lungs and one to pump oxygenated blood through the body's circulatory system.

9 Claims, 5 Drawing Sheets

OTHER PUBLICATIONS

Schwartz, Melvyn. Principles of Electrodynamics. McGraw-Hill Book Co., Inc. 1972.
Sears, F.W. and Femanksy, M.W. University Physics. Adison-Wesley Publishing Co., 1955.

J.D. Enderle, S. Blanchard and J. Bronzino. Introduction to Biomedical Engineering. Academic Press, 2000.
Reference Data for Radio Engineers, 1956, by the International Telephone and Telegraph Corp., the Stafford Press, Inc., NY.

* cited by examiner

ARTIFICIAL HEART USING MAGNETOHYDRODYNAMIC PROPULSIONH

CROSS-RELATED APPLICATIONS

This application claims priority from Provisional Patent Application Ser. No. 60/609,164 filed Sep. 10, 2004.

BACKGROUND OF THE INVENTION

1. Field of the Invention

The present invention relates to man-made devices to replace the natural heart. The invention relates more specifically to a magnetohydrodynamic artificial heart which pumps human blood without using moving parts.

2. Background Art

Each year an estimated 400,000 Americans suffer from end-stage heart disease. However, only about 3,000 human hearts become available each year for transplantation. There are several industry sources that produce artificial hearts which could be used for transplantation, but all of these artificial heart designs depend on mechanical approaches for operation in conjunction with internal and external prime-power sources that provide only a limited time of operation before recharging or replacement is required. Examples of prior patents that relate to artificial heart replacement devices or to natural assist devices, include the following:

| | |
|---|---|
| 3,568,214 | Goldschmied |
| 3,768,931 | Willis Jr. |
| 3,874,002 | Kurpanek |
| 4,152,785 | Shumakov et al |
| 4,599,083 | Perlov et al |
| 4,621,617 | Sharma |
| 4,650,485 | Della Sala |
| 4,869,656 | Della Sala |
| 6,074,365 | Hahndel et al |
| 6,123,724 | Denker |
| 6,251,061 | Hastings et al |

U.S. Pat. No. 4,152,785 to Shumakov et al disclose an artificial heart for clinical and experimental conditions and having dimensions which correspond to a natural heart. This device is apparently designed to work with external working media and pumps.

U.S. Pat. No. 4,599,083 to Perlov et al disclose an artificial implantable heart which employs a plurality of permanent magnets and an electromagnetic field to move a diaphragm to pump blood. A similar device designed as a natural heart assist device is disclosed in U.S. Pat. No. 6,123,724 to Denker.

U.S. Pat. No. 6,074,365 to Hahndel et al disclose a blood pump which employs a magnetofluid-supported electromagnetic drive and an elastic membrane.

U.S. Pat. Nos. 4,650,485 and 4,869,656 to Della Sala discloses another form of ferromagnetic-fluid pump using an oscillating membrane.

U.S. Pat. No. 3,874,002 to Kurpanek discloses use of cobalt rare-earth magnets to move elastic diaphragms in response to bistable electro-magnetic pumping action. U.S. Pat. No. 3,768,931 to Willis Jr. discloses a similar concept.

U.S. Pat. No. 6,251,061 to Hastings et al disclose an assist device comprising a compressor using a ferrofluid to compress opposite sides of the natural heart. Another type of electromagnetic compressor is shown in U.S. Pat. No. 4,621,617 to Sharma.

U.S. Pat. No. 3,568,214 to Goldschmied discloses an artificial heart pump which employs an electrically conductive fluid and a pulsating magnetic field to move the fluid back and forth as a pumping device using deformable sheets or diaphragms to propel blood.

One of the principal disadvantages of these prior art designs is that they employ moving parts. Moving parts imply friction, wear and fatigue which further imply limited periods of reliable use. Repair or replacement of an artificial heart or heart assist device, requires further major surgery beyond the original installation procedure. Such surgery means use of a heart lung bypass machine and an extensive period of time for the patient to be under general anesthetic. Of course, it also implies entry into the chest cavity and an extensive period of pain and discomfort to recover from the surgery, as well as the need for pain medication and the use of drugs to ward off infection and stroke. Moreover, moving parts can cause dangerous blood clotting that can travel through the circulatory system and cause other problems such as stroke.

Therefore, there is an ongoing need for an artificial heart apparatus or heart assist apparatus which is inherently more durable and more reliable than existing designs. It would be highly advantageous if it were possible to provide such a device implemented in a manner which obviated all moving parts.

SUMMARY OF THE INVENTION

The present invention, in its preferred embodiment, comprises an implantable artificial heart apparatus which has no moving parts. It employs the technology of magnetohydrodynamics (MHD) to induce flow of human blood. MHD involves the direct interaction between magnetic and electric fields and a conductive fluid. Blood is a fluid that transports nutrients throughout the body. Blood can be considered to be connective tissue containing cells, proteins and inorganic ions, all carried along in a fluid plasma. From an electrical point of view, blood can be classified as an electrolytic fluid. If blood were to carry an electric current, the transport mechanism would be classified as an ionic transport process, one that is amenable to magnetohydrodynamic propulsion. Such propulsion is achieved in the preferred embodiment by an MHD propulsion unit. An MHD propulsion unit is a device which applies magnetic and electric fields to blood to propel the conductive fluid through the body's circulatory system. Electricity is passed through the blood via electrodes at the same junction where the blood is exposed to the magnetic field. Charged ions that move from anode to cathode create their own corresponding magnetic fields which are either attracted or repelled by the externally applied magnetic field. The result is propulsion in a uniform direction with the moving ions, in effect, dragging fluid molecules with them. A single MHD propulsion unit performs the combined functions of the atrium and the ventricle of the human heart. Two MHD propulsion units are required to perform the full cardiac cycle of the heart, one to pump unoxygenated blood through the lungs and one to pump oxygenated blood through the body's circulatory system.

In the preferred embodiment of the invention, the electric and magnetic fields are powered by an external power unit, the output of which is coupled through the chest wall by transcutaneous induction.

The resulting artificial heart will provide the following significant features:

1) Low weight reduces anchoring and structural load effects due to external body accelerations;

2) Primer power is inductively coupled to internal electronics and drive circuits through a patient interface power control unit;
3) No internal batteries are required;
4) Battery replacement is performed outside of the patient's body;
5) No skin penetrating interfaces, avoids potential for infection;
6) Superior monitoring of pump operation;
7) No moving parts;
8) Controllable transfer function to avoid damage to connecting vasculature tissue;
9) Readily scalable to accommodate patient size; and
10) Easily programmed to provide appropriate blood pressure.

BRIEF DESCRIPTION OF THE DRAWINGS

The aforementioned objects and advantages of the present invention, as well as additional objects and advantages thereof, will be more fully understood herein after as a result of a detailed description of a preferred embodiment when taken in conjunction with the following drawings in which.

DETAILED DESCRIPTION OF A PREFERRED EMBODIMENT

Figure 1A:
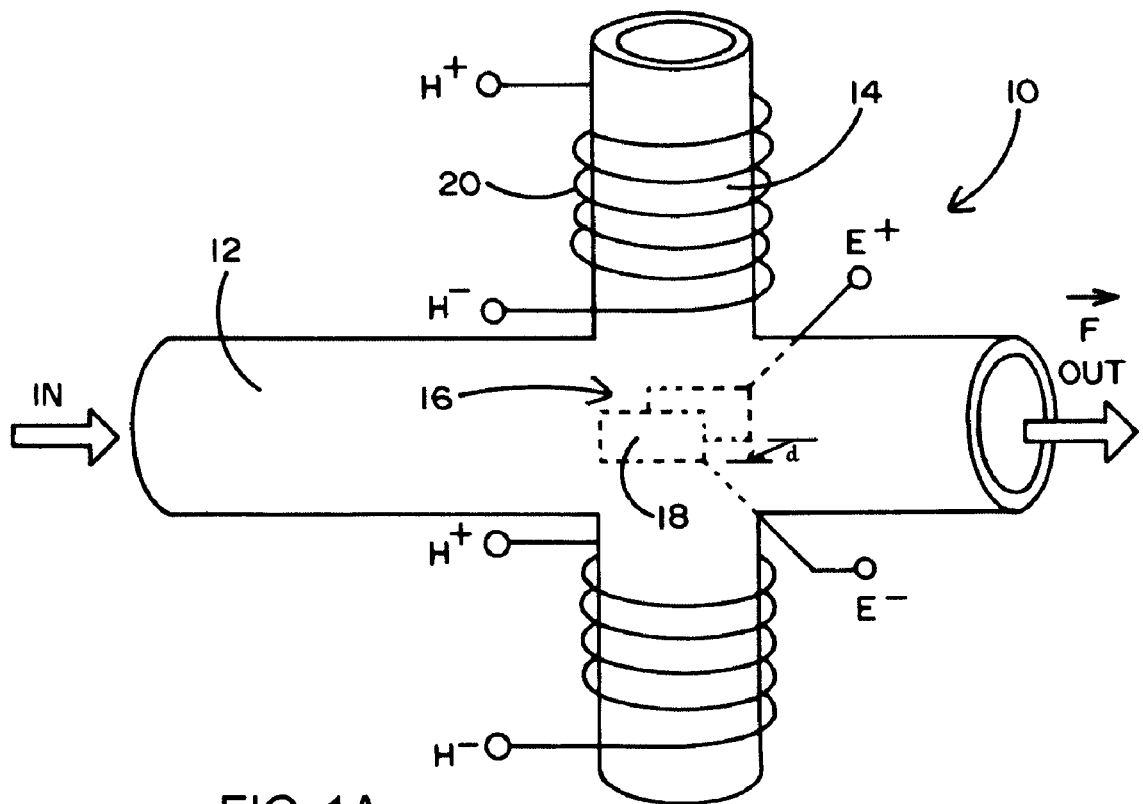
FIG. 1A is a conceptual illustration of a propulsion unit of the invention.
Figure 1B:
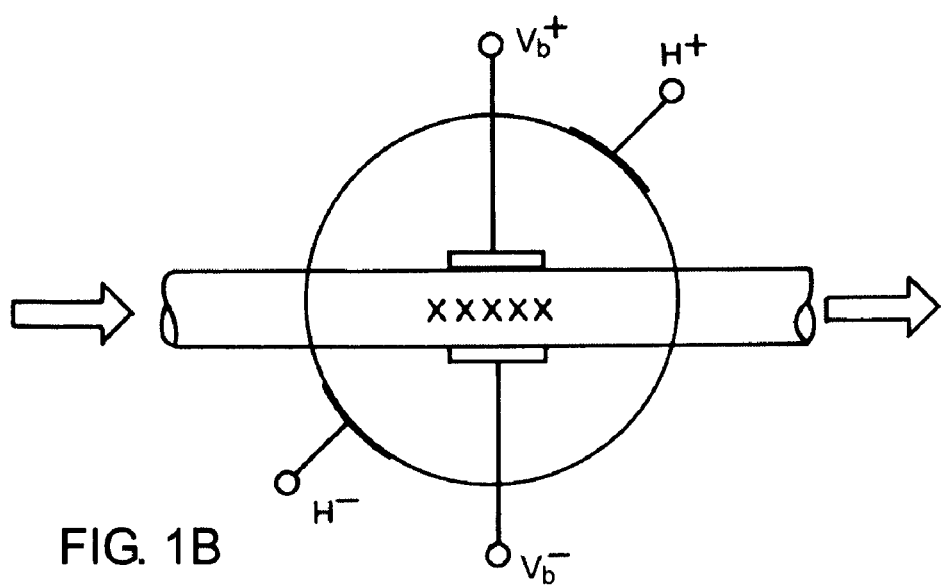
FIG. 1B is a drawing of the electrical symbol for a propulsion unit.

Referring to the accompanying drawings and initially to FIGS. 1(a) and 1(b), it will be seen that a propulsion unit 10 comprises a flow tube 12 and a coil core 14. The tube 12 and core 14 intersect at an interactive chamber 16 in which there are located at least two electrode plates 18 for generating an electric field within chamber 16 which field is perpendicular to the direction of flow through tube 12. Each side of core 14 is wound with an inductive coil 20 to generate a magnetic flux field within chamber 16 that is orthogonal to both the direction of flow and the electric field. The resulting propulsion force $\vec{F}$ is given by the equation:

$$\vec{F} = nq\vec{vd} \times \vec{B}$$

where n=number of charge carriers; q=electric charge, e=$1.602 \times 10^{-19}$ Coulombs, vd=drift velocity of charge carriers across a voltage gradient $\vec{E} = -\vec{\nabla}V$; $\vec{B}$=magnetic flux density vector $\vec{B} = \mu_0 \vec{H}$ where $\mu_0$=permeability of freespace, $\mu_0 = 4\pi \cdot 10^{-7}$ H/m; $\vec{H}$=magnetic field intensity vector, $\vec{F}$=force vector produced at right angles to both electric and magnetic fields and V=the voltage applied to the electrodes of the electric drive.

FIG. 1B shows the schematic symbol used herein to represent a propulsion unit according to FIG. 1A.

Figure 2:
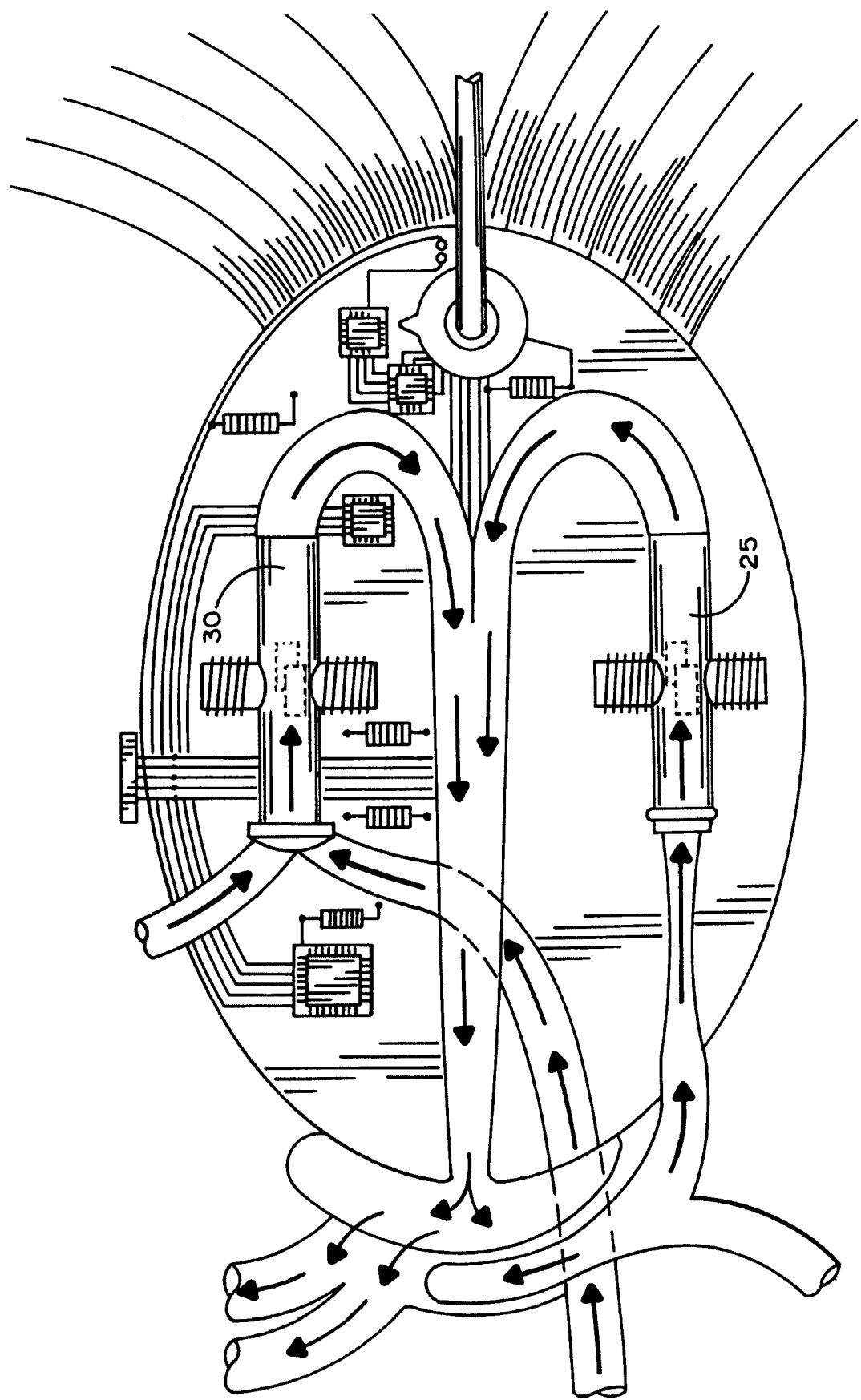
FIG. 2 is a mechanical diagram of an artificial heart in accordance with a preferred embodiment of the invention.

FIG. 2 is a conceptual illustration of two propulsion units 25 and 30 in the chest cavity after removal of the natural heart. Propulsion unit 25 serves as the equivalent of the right side of the natural heart and propulsion unit 30 serves as the equivalent of the left side. Propulsion unit 25 is connected to the pulmonary circulatory system through the pulmonary artery. Propulsion unit 30 is connected to the systemic circulatory system through the aorta. Propulsion unit 25 receives waste-rich blood through two large veins called vena cavae. Propulsion unit 30 receives oxygen enriched blood from the lungs. Because an MHD pump is a continuous flow device, there is no "beating" or rise and fall of pressure as with a natural heart. Consequently, there is no back pressure which would otherwise create a backward flow of blood if there were no one-way valves in the natural heart. Accordingly, the artificial heart of the present invention does not require valves. Consequently, each propulsion unit 25, 30 functions as both atrium and ventricle of the natural heart for the respective side or respective circulation system (i.e., pulmonary versus systemic).

Figure 3:
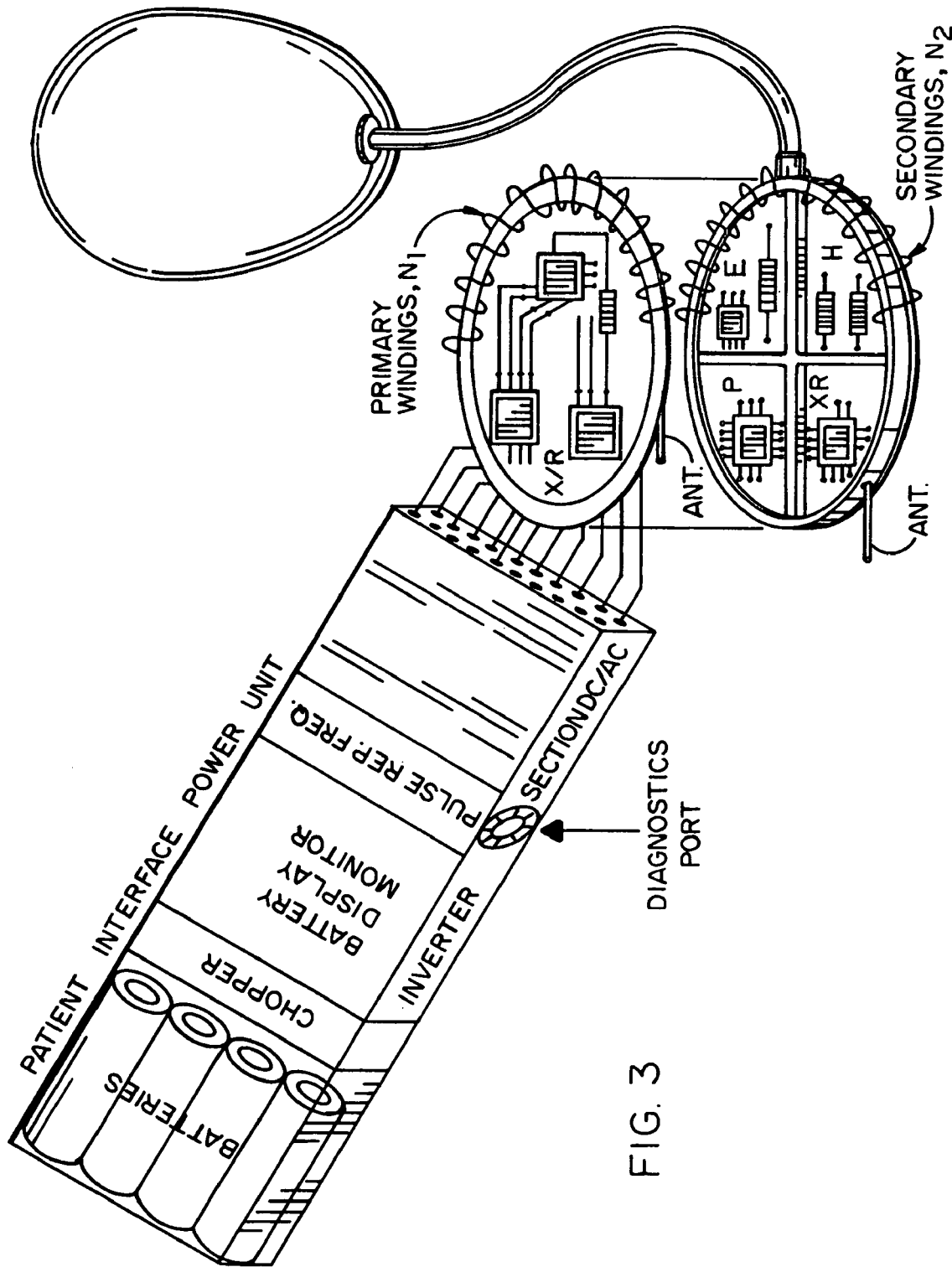
FIG. 3 is a pictorial illustration of a complete operational heart system in accordance with the preferred embodiment.

FIG. 3 illustrates the remaining portions of the system of the present invention. The artificial heart of FIG. 2 is connected within the patient to an implanted power pick-up sensor which is preferably located close to the rib cage. An externally positioned patient interface power unit may be preferably supported in position by a vest-like unit that is worn around the patient's chest. The power is supplied by a power unit which includes a transcutaneous interface pack residing in external juxtaposition to the implanted power pick-up sensor. Other components of the patient interface power unit include a battery pack, battery status display monitor and diagnostic port.

Figure 4:
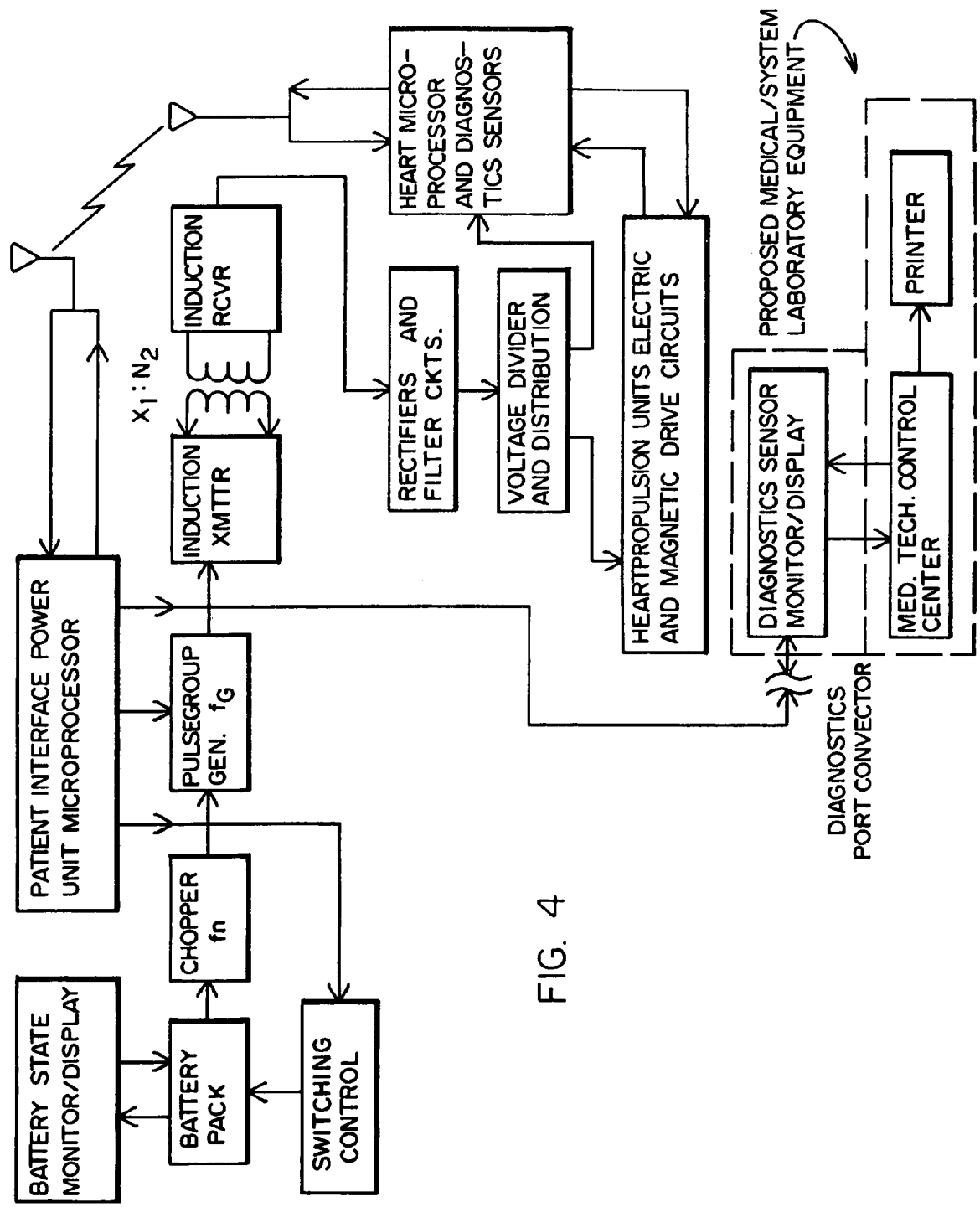
FIG. 4 is a block diagram of the system of FIG. 3.

FIG. 4 is a block diagram of the artificial heart system of the preferred embodiment. As shown therein, the external-to-internal interface comprises an external induction transmitter and an internal induction receiver. In order to employ transcutaneous induction, the DC output of the battery pack is chopped by a chopper which produces an output fed to a pulse group generator fed to the induction transmitter. The output of the induction receiver is rectified and filtered and then fed to voltage divider and distribution circuits which feed the electric and magnetic drive circuits of the propulsion units. The output of the voltage divider and distribution circuits also power microprocessor and diagnostic sensors which monitor the performance of the propulsion units. These sensors communicate with an external power unit microprocessor by means of a wireless interface which uses a conventional protocol such as 802.11(a) through a small dipole antenna secured to the implanted power pick-up sensor housing or other suitable anchor point and a matching antenna on the patient interface power unit. The external microprocessor feeds the diagnostics monitor/display and optional external monitoring devices through the diagnostics port.

Figure 5:
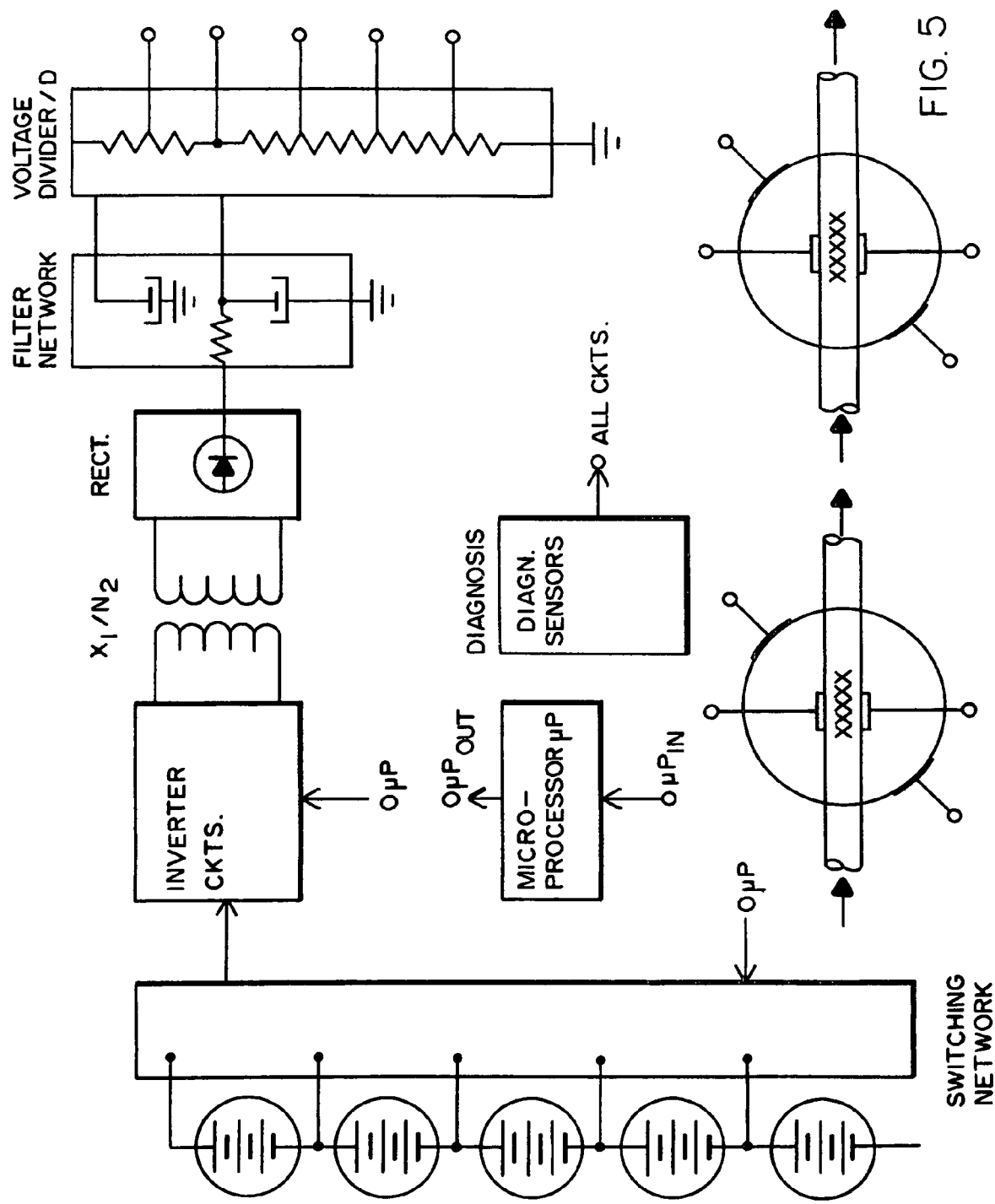
FIG. 5 is a top level circuit diagram of the heart system.

FIG. 5 illustrates the switching and filtering circuits on each side of the transcutaneous induction interface.

The medical profession has stated that "mechanical" artificial hearts damage the connecting vasculature tissue which connects the heart to the patient's body as a result of the "shape effects" of the ECG waveform produced by the mechanisms of those artificial hearts. Now, since the present heart is fundamentally an electronic circuit it can have the various "transfer functions" of the circuits designed such that they produce an "output" pulse (ECG) that represents a time-function (the pressure pulse) that when examined in the frequency domain, contains all the necessary "harmonics" to represent a "high fidelity" pulse. Therefore, the heart that is described herein can be said to be a "high fidelity" heart that eliminates one of the problems identified by the medical profession when addressing conventional (mechanical) artificial hearts. The physical structure/nature of this heart allows for applications of "scaling laws" that can be invoked to produce physically small or physically large hearts so as to accommodate children as well as adults for implementations. This also goes hand-in-hand with the ability to "program" the proper systolic and diastolic blood pressures in accordance with the dictates of the attending physician.

Having identified the base technology as MHD, it is now necessary to define the characteristics of the fluid which is to be moved. Consequently, let us first examine the nature/structure and properties of human blood: Blood is defined to be connective tissue consisting of cells, nutrients, inorganic ions, all immersed in a watery fluid called the plasma. Therefore, from an electrical point-of-view, blood can be considered as an electrolytic fluid with a specific volume conductivity. Hence, if blood were to carry an electric current, the transport mechanism would be considered as purely ionic. As a result, we need to establish the proper operational environment that can influence the ions to move in a specific direction. Now, from electromagnetic field theory, we know that a charge q moving in the direction of a velocity vector $\vec{v}$ which traverses a magnetic field, $\vec{H}$ experiences a force $\vec{F}$ such that the force is orthogonal to both the v and H vectors. Thus, in vector notations we then have that $\vec{F} = q\vec{v} \times \vec{B}$, as denoted by the conventional vector "cross-product", recognizing that the force $\vec{F}$ bears a "spatial" relationship among the field quantities, $\vec{v}$, $\vec{H}$ and $\vec{F}$.

It is evident that any mechanism that may be fabricated to move the blood must preserve those spatial relationships. In addition, the mechanism must produce the required motion or acceleration of charges (the ions in the blood) which must then move in the presence of a uniform magnetic field. We have selected the configurations shown in FIG. 1A to provide the necessary environment to develop the force $\vec{F}$. We shall call the physical structure of FIG. 1A, a PROPULSION UNIT, or "PPU". FIG. 1b also shows a symbol to represent the unit. The symbol is reminiscent of the vacuum-tube symbology used in describing electronic architectures. We shall use it to describe specific configurations of the heart proper.

Now, the acceleration of the charges is obtained by using a pair of electrodes within the active region of the flow tube, thus forcing the ions to accelerate through a potential drop of an electric field along the x-axis, given by $\vec{E_x} = -\nabla V_b$ where $V_b$ is the scalar potential difference between the electrodes, and $\vec{\nabla}$ represents the "del" operator of vector calculus. The potential $V_b$ produces a current is such that $$i_b = \frac{V_b}{R_v} = nq v_x,$$

where $R_v$ represents the volumetric resistance of the blood, measured in ohms/cm³, $v_x$ the velocity, q=electron charge=1, $602.10^{-19}$ coul., and nq is than the total number of charges transported across the electrodes and represents the measurable current produced by the electric drive of the propulsion unit.

Since it is known that the magnetic field produced by a solenoid is uniform and homogeneous, then we choose to use a pair of co-linearly wound solenoid coils along the y-axis, as shown in FIG. 1A.

Now that we have identified a physical structure to propel the blood, we need to obtain the analytical equations which will allow us to derive the design parameters of the PPU, or propulsion unit.

Analysis of Charge Particles Moving in Crossed Electric and Magnetic Fields

When a group of point charges nq moves in the presence of a combined electric $\vec{E}$ and a magnetic field, $\vec{H}$ the group of charges experiences a force from each of the fields. Since the system is linear then superposition holds, and the total force $\vec{F}$ is given by the sum of those two forces such that $$\vec{F} = nq\vec{E} + nq(\vec{v} \times \vec{B}) \tag{1}$$

where $\vec{v}$ = the velocity of the charges in mtr/sec $\vec{B}$ = magnetic flux density in ubr/mtr² and $\vec{B} = \mu_0 \vec{H}$ = permeability of free-space and $\mu_0 = 4n \cdot 10^{-7}$ hy/mtr.

n = a positive integer $n \geq 1$.

But, the total force is also given by $\vec{F} = M\vec{a}$ for an acceleration $\vec{a}$, or, in terms of the time-rate-of-change of linear momentum, $$\vec{F} = \frac{d}{dt}(m\vec{v}).$$

It is valid to assume that the mass is constant and independent of the velocity. Let us first look at the equations of motion due to the electric field. Thus, Equation No. (1) above in terms of the position coordinates, x, y and z, gives the components of the force as:

$$F_x = nqE_x = M\frac{dV_x}{dt} = M\frac{d^2 x}{dt^2} \tag{2}$$

$$F_y = nqE_y = M\frac{dV_y}{dt} = M\frac{d^2 y}{dt^2} \tag{3}$$

$$F_z = nqE_z = M\frac{dV_z}{dt} = M\frac{d^2 z}{dt^2} \tag{4}$$

Now, integrating Equation No. (2) gives, $mv_x = nq E_x t + C_1$, where $C_1$ is the constant of integration. Utilizing the initial conditions as the boundary conditions, where at time=0, the velocity $v_x$ is zero, yields $C_1 = 0$ also, and then we can write the equations for the velocity $v_x$, as a function of time. Hence, $$v_{x(t)} = \frac{nq}{M}E_x t.$$

Now, since according to FIGS. 1A and 1B, we can see that $$E_x = \frac{V_b}{d},$$

we then have $$V_{x(t)} = \frac{nqV_b}{Md} t \quad (5)$$

It is apparent that Equation No. (5) is in the standard form for the equation of a straight line with a slope of $$\frac{nqV_b}{Md}$$

and of zero intercept.

Now, the time needed by a charge to transverse the miterelectrode distance, d, is given by $$t_d = \frac{d}{V_x}$$

seconds.

Therefore, Equation No. (5) gives a velocity $$v_x = \frac{nqV_b}{Md}\left(\frac{d}{V_x}\right), \text{ or} \quad (6)$$

$$V_x^2 = \frac{nqV_b}{M} \text{ and thus,}$$

$$V_x = \left[\frac{nqV_b}{M}\right]^{1/2}$$

Now that we have the velocity of the charges, we need to account for the contribution from the magnetic field to the total force. However, before we look at the second term of the right-hand side of Equation No. (1), let us define the vectors that we need to use, with the specific notations of vector calculus: In general, any vector $\vec{V}$ will be given by its component parts such that in Cartesian coordinates we have $\vec{V}=V_x\vec{1_x}+V_y\vec{1_y}+V_z\vec{1_z}$. Similarly, another vector such as the magnetic flux density vector can be represented by $\vec{B}=B_x\vec{1_x}+B_y\vec{1_y}+B_z\vec{1_z}$. We have utilized one of the conventional ways of defining a unit vector by using a numeric one (1) properly subscripted and with the identifying overscripted arrow. Thus, $\vec{1_y}$ represents a unit vector in the y direction. Since by definition, all unit vectors have unit "magnitude", this convention, will keep us reminded of that fact. We shall consistently use that convention while the "components" of a vector are only subscripted. For example, the quantity $B_z$ represents the components of the flux density vector along the z-axis and is purely "scalar" quantity.

Now, to find the contribution from the magnetic field to the total force on the charge, let us look at the second term of the right hand side of Equation No. (1) which expresses the cross-product of $\vec{V}$ and $\vec{B}$ and is given by $\vec{F}=nq(\vec{V}\times\vec{B})$. As stated previously, in general, we have $\vec{V}=(v_x\vec{1_x}+v_y\vec{1_y}+v_z\vec{1_z})$ and $\vec{B}=B_x\vec{1_x}+B_y\vec{1_y}+B_z\vec{1_z}$. From the fundamental definitions of the vector cross-product, it is possible to show that $\vec{F}=nq(v\times\vec{B})=nq\{(v_yB_z-v_zB_y)\vec{1_x}+(v_xB_z-v_zB_x)\vec{1_y}+(v_xB_y-v_yB_x)\vec{1_z}\}$. Now, we have found that: the velocity vector has only a component in the x-direction as produced by the accelerating potential $v_b$, along the x-axis, and is given by Equation No. (6). Also, the magnetic drive coils produce an axial flux density, $B_y$, which, is a field along the y-axis. Substituting all the vector components into the above expressions, gives a force $$\vec{F}=nq(V_xB_y)\vec{1_z} \quad (7)$$

which is purely along the z-axis, as expected. Now, we have enough equations to begin our design calculations in the next section.

Design Calculations and Derivation of The Parameters for a Propulsion Unit

Let us now work to obtain the blood pressure expression that applies to the propulsion unit. For that purpose we need to first identify all the physical parameters that govern the architecture of the unit. Those parameters are also shown in FIG. 1A, and also apply to Equation No. (1) below as well. The magnetic drive will consist of two solenoids co-axially aligned along the y-axis. The flux density that they will generate is obtained from Ampere's law and/or the Bio-Savart law which yields $$B_y = \mu_0 \frac{N_L i_L}{L} \quad (1)$$

Definition of Parameters:
- d=inter-electrode spacing measured along the x-axis
- $d_{fi}$=inside diameter of flow tube
- $d_{fo}$=outside diameter of flow tube
- L=length of solenoids measured along the y-axis
- $L_f$=half-length of the flow tube from the origin to either end
- $h_b$=opening of coils which determines the magnetic flux area coverage. This is the coverage across the active region. Also, equals the length of the electrodes along the axis.

Propulsion Unit (PPU) Identifying Parameters and Definitions

- $N_L$=number of turns for the two solenoid coils combined in series (TOTAL NL)
- $i_L$=current through the magnetic drive coils
- $A_f$=cross-sectional area of flow tube
- $i_b$=current produced by the electric drive
- $V_b$=operating potential for the electric drive electrodes
- $V_L$=operating potential for the magnetic drive coils We can now define the "active region" of the propulsion unit as a cylindrical volume $\Psi_a$ bounded by the electrodes, such that $$\psi_a = \frac{\pi d^2 h_b}{4}. \quad (2)$$

Therefore, for a blood density of $\rho$, we have a mass m given by $M=\rho\Psi_a$, or $$M = \frac{\rho d^2 h_b}{4}. \quad (3)$$

It can be seen that the fluid (blood) moves in volume units of mass m, with each mass unit being followed by another one, thus creating a uniform flow of blood. The uniformity of flow must also be supported by the "homogeneity" of the magnetic flux across the active region. Therefore, the solenoid coils must be wound with the same "sense" and "direction" in order to obtain the correct magnetic north-south (N to S) polarity across the active region. As noted before, the axis of the solenoids is along the y-axis of the propulsion unit. It is convenient at this time to gather all the analytical expressions and place them in a single location to facilitate the derivation of a unified expression seeded in the design of the propulsion unit (PPU). This is accomplished with Table 5-1, where all the previous equations have received new numbers, all in sequential order.

TABLE 5-1

ANALYTICAL EQUATIONS NEEDED FOR THE DESIGN OF THE PROPULSION UNIT (PPU)

$$V_x = \left[\frac{nqV_b}{M}\right]^{\frac{1}{2}} \quad (1)$$

$$\psi_a = \frac{\pi d^2 h_b}{4} \quad (2)$$

$$F_z = nqV_x B_y \quad (3)$$

$$M = \frac{\rho d^2 h_b}{4} \quad (4)$$

$$B_y = \mu_0 \frac{N_L i_L}{L} \quad (5)$$

When considering the nature of all the parameters above, we have some design freedom in establishing the values of some of these parameters since many are dimensional in nature and are established by how much space is available within the physical structure of the heart proper. However, a parameter such as $N_L$, the number of turns needed for the solenoids, has to be solved explicitly in accordance with the magnitude of the blood pressure desired and/or required. The following Table 5-2 is provided as a guideline when establishing appropriate parameter values.

Table 5-2

Important Parameters, Data and Values Surrounding the Physiology of the Human Head (See Reference 4 Below—The Pages Shown within Parenthesis Apply to Reference 4)

Size of the human heart, L×W=12×8 cm (pg. 491)
Weight of heart=0.75 lbs.
Diameter of aorta at its base=2.8 cm (pg. 502)
Density of blood $\rho$=1.07 gm/cm³ (pg. 472)
Stroke power needed to sustain life: (pg. 499)
  (a) during sleep or very relaxed=5 watts
  (b) during peak loads=12 watts for brief periods
  (c) sedentary work=4 watts Let us now strive to obtain an expression for $N_L$. From the equations in Table 5-1, we need to first obtain an expression for the force, F. Thus, using Equation No. (3), we have $F_z = n_q v_x B_y$. But, since $i_b = n_q v_x$, then $F_z = i_b B_y$. Then, using Equation No. (5), $$Fz = \frac{\mu_o N_L i_L i_b}{L} \quad (6)$$

Let us now assign some values to the parameters of Equation No. (6):
Let: $L=5 \cdot 10^{-3}$ mtr (based on dimensions of the heart proper (L×W), (12 cm×8 cm), and the space available for the 2 PPUs, flow tubes, et cetera
Also let:
$L=5 \cdot 10^{-3}$ mtr
$i_b$=100 ma
$i_L$=100 ma
Then substitution into Equation No. (6) gives $$F = \frac{(4\pi \cdot 10^{-7} N_L)(10^{-1})(10^{-1})}{5 \cdot 10^{-2}} = 2.51 \cdot 10^{-6} N_L \quad (7)$$

Now again, considering the cross-dimensions of the heart, let us chose a flow-tube diameter $d_{fl}=2 \cdot 10^{-3}$ mtr. Then, its cross section area $A_f$ becomes $$A_f = \frac{\pi d_{fl}^2}{4} = \pi \frac{4 \cdot 10^{-6}}{4} = \pi \cdot 10^{-6} M^2$$

For the heart to generate a "systolic" pressure of 140 mmHg, or its equivalent in MKS units, $P_b$=1.86·10⁴ Pasc. Using the flow-tube as above with cross-section $A_f=\pi \cdot 10^{-6}$ M², requires a force $\vec{F}$ along the tube axis of $F_z=P_b A_f=1.86 \times 10^4$ $(\pi \cdot 10^{-6})=5.8 \cdot 10^{-2}$, and this must also be the same force required to be produced by Equation No. (7). Therefore, we can say that $2.51 \cdot 10^{-6} N_L = 5.8 \cdot 10^{-2}$ which gives $N_L = 2340^3$ turns.

This is the total number of turns for both coils in series. Let us now calculate the total wire needed, the resistance, and the weight of the copper used.

With a coil diameter $h_b$=1.5 cm the circumference $C_L=\pi_{hb}$=4.7·10⁻² mtr. The total wire length lT is then lT $=N_L C_L$ which gives lT =1.08·10³ mtr or, in feet, lT =3.54·10³ ft.

Now, using the data from reference 5, for enamel coated annealed copper wire of No. 37 ANG, we have a resistance per foot, $$r' = 523.1 \cdot 10^3 \frac{\Omega}{ft}.$$

Therefore we have a resistance given by R=r'lT =1.8·10³Ω. Hence, in order to produce the magnetic drive current of 100 ma, we need an operating potential of $V_L=R_{coil} \times 10^{-1}$=180 volts. This is an attainable voltage from the patient power source, as will be seen in the following section. Then, the weight of the coils is given as $$W_L = W l_T, \text{ where } w' = 0.06 \cdot 10^{-3} \frac{lbs}{ft}.$$

Thus $W_L = 3.54 \cdot 10^3 (0.06 \times 10^{-3}) \frac{lbs}{ft} = .2124$ lbs.

Note that this weight represents the majority of the weight associated with the PPUs. The remaining contributions to the unit's maximum weight will come from the various tubes and connectors from the flow tube to and from the blood vessels of the patient's body. Thus, we can assign a weight budget of 0.352 lbs. to meet the target weight of 0.75 of the natural heart.

Now that we have obtained a general definition and design of the physical characteristics of the heart we need to determine the volumetric output from the heart. To that end we first need to know the linear velocity of the blood at the output of the flow tube of the propulsion unit. Now, we know that using the parameter values described previously, the volume of the active region $\Psi_a$ is $$\Psi_a = 1.06 \cdot 10^{-7} \text{ mtr}^3 = 1.06 \cdot 10^{-1} \text{ cm}^3$$

Also from reference 4 we are given the density of blood, $\rho$, as $$\rho = 1.07 \frac{gm}{cm^3} = 1.07 \cdot 10^{-9} \frac{kg}{mtr^3} \quad (8)$$

We had also obtained a force $F_z = P_b A_f = 5.8 \cdot 10^{-2}$ mtr when we used a systolic design target figure of 140 mmHq. for the blood pressure $P_b$. The volume $\Psi_a$ represents the quantity of blood filling the active region, ready for propulsion. Therefore, for every electric drive pulse a new $\Psi_a$ volume travels along the flow-tube axis. Therefore, the energy $E_R$ required to move a mass unit of blood $m = \rho \Psi_a$ through a distance $h_b$ within the active region becomes $E_R = F_z h_b$ and this value must also be equal to the kinetic energy required/involved in the process.

Hence, $$F_z h_b = \frac{1}{2} M V_z^2 \text{ which yields } V_z = \left[\frac{F_z h_b}{M}\right]^{1/2} \quad (9)$$

substitution of the appropriate values into Equation No. (9) gives $v_z = 3.9 \cdot 10^6$ mtr/sec.

The very large value of velocity represented by Equation No. (9) is characteristic of the values often encountered in electron ballistics problems. With such a velocity a charged particle will then "dwell" in the active region for a period of time, $t_d$ $$\text{given by } t_d = \frac{h_b}{V_z}, \text{ or} \quad (10)$$

$$t_d = \frac{1.5 \times 10^{-2}}{3.9 \times 10^6} = 3.8 \times 10^{-9} \text{sec}.$$

Therefore, when applying a pulse or a pulse train to the electric drive, each of the pulses must have a width greater than $t_d$.

Then, for a pulse repetition frequency prf=fr, measured in pulses per second, the volumetric output from the heart becomes $$\Psi_o^1 = \Psi_a \text{fr} \quad (11)$$

Conversely, we can also find the prf necessary to satisfy a specific design value for a given coronary output $\Psi_o^1$. That is $$fr = \frac{\psi o^1}{\psi a} \quad (12)$$

Now, the values for the system and pulmonary volumetric output rates of the natural heart are independent and different. From reference 4, (page 513, table 10.7) we have:

The systemic output at the aortic value $$\psi_0^1 L = 5,345 \frac{cm^3}{min} = 89.08 \frac{cm^3}{sec}$$

The pulmonary circulation has a value of $$\psi_{OR}^1 = 5,184.65 \frac{cm^3}{min} = 86.41 \frac{cm^3}{sec}$$

at the pulmonary valve

Therefore, we will need two different values of prf, fr to satisfy the requirements of the natural heart, to satisfy the requirements of the natural heart.

Thus, for the left side PPU, the prf is $$fr_L = \frac{\psi_{oL}^1}{\psi_a} = 840 \text{ pps}.$$

Then for the right side PPU, the prf is $$Fr_R = \frac{\psi_{or}^1}{\psi_a} = 815 \text{ pps}.$$

It is encouraging to see that we have been able to obtain very reasonable operating parameter values that allow our heart design to match those of the natural heart and thus predict equivalent performance.

Now that we have a design definition with performance figures for the heart, we need to determine the necessary physical volume and space requirements needed for its implementation/realization. It is convenient at this time to summarize all the physical dimensions and values used throughout this disclosure. Table 5-3 provides such data.

TABLE 5-3

DIMENSIONS, SYMBOLS AND VALUES UED THROUGHOUT THE PAPER

| | |
|---|---|
| d = | $3 \cdot 10^{-3}$ mtr |
| $h_b$ = | $1.5 \cdot 10^{-2}$ mtr |
| $d_{fi}$ = | $2 \cdot 10^{-3}$ mtr |
| $A_f$ = | $\pi \cdot 10^{-6}$ mtr2 |
| L = | 1 cm |
| $d_{fo}$ = | 0.5 cm |
| $2L_f$ = | 8 cm |

Using the values above we can determine the area or "footprint" for a PPU, as A=1.5 cm×8 cm=12 cm$^2$. Let us now define an area equal in size to the area of the natural heart (12 cm×8 cm, L×W) where we have reserved five areas, $A_1$ to $A_5$. The two PPUs occupy areas $A_1$ and $A_2$, while area $A_3$ is reserved for the electronics such as a microprocessor (µp), integrated integrate circuits (ic), sensors, several resistors, memory and other discretes that may be needed as the heart design begins its transition into a Smart Heart Operation.

Areas $A_4$ and $A_5$ are reserved as open passages for extension tubes that will allow for connection from the PPUs to the blood vessels of the patient. In summary, we have allocated 64 cm² of space for the various components, from an available 96 cm² for the total heart area of the natural heart.

It is recognized that the ultimate configuration of the heart enclosure will be different than the simple rectangular configuration, and would require a design effort of its own to provide an optimum enclosure. Nevertheless, it becomes apparent that we can provide space for the necessary components which can perform all the functions of the natural heart in a space compatible with that of the natural heart. This can only help in the implementation procedure and can only be of benefit to the patient. It is instructive at this time to examine the illustration shown in FIG. 2. That illustration was made at a very early stage in the conceptualization of the physical size of the PPUs so that what FIG. 2 shows is an arbitrarily large size of the PPUs. Nevertheless, the figure does indicate the "computer-like" architecture of the heart. This figure also gives an indication of the positions of the heart in the thoracic cavity of the person. An addition feature depicted in the figure is the presence of a "resparation sensor" which rests against "plura" or envelope that surrounds the lung and can thus monitor the intensity and rate of motion of the lung as the person breaths. This sensor can be a MEMS, (Micro-electro-mechanical sensor) or a silicon micro-machined accelerometer "chip". In either case, this represents information that can be transferred to the microprocessor (µp) of the heart to provide information for the control of the two prf generators that will adjust the volumetric output of blood in accordance and the needs of the patient. This is one of the many ways by which the heart begins to transition into a Smart Heart Operation, as it responds to the needs of the person.

The Power Coupler Unit

We now need to provide design definitions for a power supply/coupler unit that will generate all the operational potentials needed for normal heart operation. At present, the most advanced artificial hearts available today use internal rechargeable batteries to provide continuous operation, and all of them use the batteries to drive mechanical energy conversion devices such as pumps and motors to provide the appropriate circulation. However, because of the energy needs of those mechanical devices, the batteries can only operate for a relatively short time (for example, 30 minutes), before a recharging cycle has to begin. Since a discharged battery cannot be recharged instantaneously, the patient has to be tethered to a battery charger for the 2 or 3 hours needed so that the heart can then operate for another 30 minutes, only to again repeat the cycle. In addition, the patient is still faced with the fact that invariably, a rechargeable battery will "ultimately" refuse to accept a charge and therefore the patient then faces a surgical procedure to replace an exhausted battery. Although such operations may be regarded as somewhat routine and simple in nature, they still require an incision that needs time to heal and provides a potential source for infection. As a result, our power supply approach will not use internal batteries, but will, instead, transfer power into the heart structure by "induction", as will be described in this section.

Following FIG. 4, we can see that there is a DC input voltage provided by a battery which is outside the body of the patient. This voltage is then applied to an inverter circuit to convert the DC input to an AC voltage which is then applied to the primary of a transformer, $T_1$, which has a multi-tapped secondary. This secondary winding is considered to be a sensor that is implemented in the patient much as is done today with pacemakers and defibrillators. The location can also be similar to the locations used for those devices. A subclavian location is typical. Now, transformer $T_1$ is a STEP-UP transformer whose secondary outputs can provide a group of AC voltages which will, in turn, undergo full-wave rectification and good filtering to provide a group of very low ripple DC operating voltages. These voltages will then be used to provide all the operating potentials needed for normal heart operation.

In the diagram there is a voltage divider which will be used to develop voltages proportional to the magnetic drive currents $i_{L1}$ and $i_{L2}$ through each of the PPUs.

An additional problem needs to be discussed at this time. It addresses the manner by which we can assure continuous flow of power to the heart. This is what gave rise to the use of internal batteries. We shall use a different approach to achieve the same result, without having to use internal batteries. We can assemble all the power supply components into a single small unit that terminates into transformer $T_1$, and whose primary can be aligned with the implemented secondary/sensor unit. The illustration provided in FIG. 3, which gives an interpretation of the power coupler unit. It can be held in position by a specially constructed "garment" such as a brassiere for a lady, or a shoulder holster for a male patient. The unit operates continuously to provide power to the heart.

To assure continuous power to the heart even in cases of emergencies, accidental events, or electronic failures, we shall take a leaf from aerospace applications and use "redundancy" —single redundancy, in this case. As such, we will propose to use a second power unit "identical" to the first one, but operating in a "STAND-BY MODE" The first unit will be called the "MASTER" and the redundant unit will be the "ALTERNATE" unit. It will have its secondary/sensor coupled to the primary of a transformer, $T_2$, which is identical to transformer $T_1$ of the MASTER unit. The secondary of $T_2$ can be implemented in a region aligned with the diaphragm and can be held in place by a wide belt or "sash" worn around the waist of the patient. Since these units are small in size, the patient should not find it difficult to adjust to wearing the two units. The way that the two units work together is as follows:

1. The MASTER unit is always fully operational and provides all the power needed to operate the heart.

2. The ALTERNATE is in the STAND-BY mode consuming very low levels of power and therefore capable of remaining in that mode for a very long period of time.

Within the heart a small oscillator/amplifier (an IC) monitors the presence of a voltage across resistor $R_1$ or $R_2$. As long as the voltage is present, it means that the MASTER UNIT is working normally, and the oscillator/amplifier will generate an output signal at frequency $f_o$ which we shall call the "PILOT SIGNAL". This signal will then be injected into one of the "taps" of the secondary of $T_2$ and will be received at the PRIMARY of $T_2$ and develops a voltage across a simple parallel resonance circuit (a "tank"), tuned to frequency, $f_o$.

This pilot signal is, in turn, monitored by the circuits of the ALTERNATE power unit and will keep the unit in its STAND-BY mode as long as the pilot signal is present. If the pilot signal disappears, it means that the MASTER unit is "off-line" and is not providing power to the heart. Then, the ALTERNATE will switch to FULL POWER OPERATION and will provide all the necessary power to the heart. At that point, the MASTER can be physically removed to correct whatever difficulty that caused it to go off-line, and can then be replaced to its operational position.

In this manner the patient will always have a fully functional heart and not have to contend with internal batteries and the various penalties associated with their presence. The entire power transfer event will be transparent to the patient and will not suffer any loss of function. It is felt that his arrangement allows the patient to achieve a level of mobility, freedom, and a better quality of life.

The DC supply for the power coupler can be obtained as a battery pack using the many configurations and specifications available with modern batteries. Today there are many suppliers of high performance batteries such as Panasonic and SANYO that can provide a wide assortment of Lithium ion batteries in small size packages. For example, SANYO has a 3-volt battery with an energy rating of 4.5 watt-hours, in a small cylindrical package of 0.5 inches in diameter by 1.25 inches in length (SANYO, #CR123A). A battery pack consisting of six such batteries side-by-side would occupy a space of only 3 inches in length by 0.5 inches in height, and when connected in series would deliver 18 volts DC to the input of the inverter of the power coupler shown in FIG. 3. After conversion into an AC voltage, we could have 18 volts AC at the primary of $T_1$. Since this transformer is a STEP-UP, we can easily obtain 180 volts AC at the full secondary of $T_1$, and since $T_1$ is a multi-tapped secondary, it is possible to obtain six individual 30 volt AC outputs that could then undergo full-wave rectifications and filtering to yield six high-quality 30 volt DC outputs for the various circuits of the heart.

With an energy rating of 4.5 watt hr for that specific battery of the example, then if we limit the primary-side current to the milliampere range ($10^{-3}$a), then it is possible to extend battery operating time by multiplying the hour-rating by the inverse figure, that is by $10^3$, and still remain within the specifications of the battery. An operating time of 1000 hours at 24 hours per day gives 41.7 days which is already a good period of operation when compared to the periods that have been reported for the mechanical heart solutions. Further control on the magnitude of the primary-side current can yield further extension of the operating time. Therefore, it is clear that a current level analysis should form part of the various "trade-offs" that need to be made so that we can provide the patient with the longest battery operating time possible before replacement is needed. Although with our design approach, battery replacement becomes a routine event of a conventional nature with no special needs, no requirements, it is still desirable to limit the frequency of the procedure to the very lowest number possible. The trade-off analyses can be based in the following: Using the battery industry definition of energy rating in watt-hours, we can write the operating time, $t_h$ as $$t_h = \frac{j_h}{v_i}$$

where $t_h$=time in hours,
$j_h$=energy rating in watt hours,
v=battery voltage, and
i=battery current drain.

Conversely, we can also solve for the load current necessary to obtain a specific number of operating hours, that is $$i = \frac{j_h}{v_{th}}$$

For example, for an operating lifetime of 4,380 hrs (6 months at 24 hrs. per day), yields a current of $$i = \frac{4.5}{3(4380)} = 0.34 \, M \text{ amps}$$

It does seem possible that this heart design could yield a long battery operating lifetime for the patient and thus provide a long worry-free period of continuous use.

Summary and Conclusions

This disclosure provides the definition and the theoretical foundation for a non-mechanical artificial heart that can be used as a replacement for the natural heart. The principle of operation is based on magnetohydrodynamics, (MHD), and the motion of charged particles in the presence of crossed electric and magnetic fields. A complete analysis of the charge motion has been provided, and it is shown that this heart meets all the performance specifications of the natural heart in terms of the volumetric output of blood for both the systemic and pulmonary circulations. It achieves the performance without the need for mechanical devices to move the blood, and in a physical size that matches the natural heart (12 cm×8 cm, L×W) and with a weight of 0.6 lbs. vs. 0.75 lbs. for the natural heart. The heart does not use "internal" batteries and the power to operate the heart is coupled by "induction" only, with the aid of two external and small power supply units that work together to supply the heart with continuous power and operation for the safety of the patient. The absence of cables, tubes, or other power-connecting devices that would pierce the skin of the patient eliminates potential sources for infection and represents a degree of mobility and freedom for the patient that provides a measure of improvement in the quality of life for the recipient of the heart. The construction of the heart consists of two propulsion units (PPUs) that provide the full circulation of a cardiac cycle. Each PPU acts as the atrium and ventricle of the natural heart and is mounted on a circuit board, or motherboard that is populated by a variety of electronic components and sensors. The construction is similar in nature to that used in the fabrication of portable (lap-top) computers, or POAs. As a result, the manufacturing capability available today in the United States can be utilized to produce this heart concept and thus obtain the high reliability and quality of such commercial units.

The applicant remembers that in the recent past it was extremely difficult to propose the use of commercial devices for aerospace or military applications. Today, however, the picture is entirely different to the extent that there is even an acronym that is used frequently: "COTS" which stands for Commercial Off The Shelf use of such devices welcomed today and many times they are even requested for military/aerospace applications. The heart design of the present invention can be considered to be a COTS item. As such, it offers several advantages. For example, the heart could be stocked in a hospital's inventory and be available for immediate implementation, thus eliminating the donor heart harvesting and the sometimes lengthy transportation time.

LIST OF REFERENCES

1. Hayt, Jr. William H. Engineering Electromagnetics. McGraw-Hill Book Co., Inc., 1958
2. Schwartz, Melvyn. Principles of Electrodynamics. McGraw-Hill Book Co., Inc. 1972
3. Sears, F. W. and Femanksy, M. W. University Physics. Adison-Wesley Publishing Co., 1955
4. J. D. Enderle, S. Blanchard and J. Bronzino. Introduction to Biomedical Engineering. Academic Press, 2000.
5. Reference Data for Radio Engineers, 1956, by the International Telephone and Telegraph Corp., the Stafford Press, Inc., NY.

Appendix

Special Safety Considerations of the Smart Heart

Introduction and Summary

The following topics (shown in "question form") are considered:

1. What temperature effects are produced on the blood as it passes through the Propulsion Unit (the PPU)?
2. What are the potential "hemolysis" effects that might be produced by the use of MHD as the basis for the production of blood circulation?
3. What is the magnetic flux level used? And, are there any detrimental effects expected?

The analyses included here provide the following answers and results:

1. The temperature effects are so small (e.g. $3 \cdot 10^{-3}$ c/hr) as to be easily disregarded.
2. The hemolysis of the red-blood cell is shown to represent, at best, a "second-order" effect on the blood in this heart design (see pages A-8 to A-10) and can also be disregarded.
3. The magnetic flux density, By is obtained by substitution of all of the quantities in equation (5) of the above description. The resulting value is $B_y=0.59$ Teslas. This value is well below the "clinical" application levels used in magnetic imaging machines and other diagnostic devices. Therefore, the flux density is considered to be a safe value with a significantly large safety margin.

Specific Analysis

Above we identified the "Active Design" denoted by 105$_a$, as a cylindrical length of the flow-tube where the electric and magnetic fields meet and cross and is given by Equation No. (2) as $$\psi_a = \frac{\pi d_f^2 h_b}{4},$$

for a flow-tube diameter of $d_f$ and electrodes of length $h_b$, measured along the z-axis.

Let us now examine that region in greater detail.

Using a flow-tube diameter $d_f=4.5$ nm, we can identify the structural characteristics of $\Psi_a$. The figure shows the "end-view" of the cylindrical structure of $\Psi_a$.

The circumference of the entire region is $C_a=\pi d_f=\pi(4.5 \times 10^{-3})=14.1 \cdot 10^{-3}$ mtr.

Now, let: $w_b=6$ mm (2 each, as the electrode width)
$w_g=1$ mm (2 each, the guard-band width)

The cross-sectional are is $$A_f = \frac{\pi d^2 f}{4} = \frac{\pi (4.5 \cdot 10^{-3})^2}{4} = 1.59 \cdot 10^{-5} mtr^2$$

Let us use a blood pressure $p_b$ of 100 mm Hq=$1.33 \cdot 10^4$ Pascals

Then, a force in the z-direction, $F_z$, would be given by $F_z=p_o A_f=1.33 \cdot 10^4(1.59 \cdot 10^{-5})=2.1 \cdot 10^{-1}$ newtons. This force must also be equal to the value given by Equation No. (6) of Section 5, as repeated here.

$$F_z = \frac{\mu_0 N_L i_L i_b}{L} \tag{6}$$

Let:
$i_L=20$ ma=$2 \cdot 10^{-2}$a
$i_b=350$ ma=$3.5 \cdot 10^{-1}$a
and L=5 mm
Then, $$F_z = \frac{4\pi \cdot 10^{-7} N_L (2 \cdot 10^{-2})(3.5 \cdot 10^{-1})}{5 \cdot 10^{-3}} 1.76 \cdot 10^{-6} N_L$$

Therefore, $$2.1 \cdot 10^{-1} = 1.76 \cdot 10^{-6} N_L, \text{ and } \frac{N_L = 2.1 \cdot 10^{-1}}{1.76 \cdot 10^{-6}} = 1.19 \cdot 10^5$$

turns.

With a coil diameter of $h_b=1.5$ cm, its circumference $C_L$, is then $$C_L = \pi h_b = (\pi(1.5 \cdot 10^{-2}) = 4.7 \cdot 10^{-2} \text{ mtr}$$

The wire length IT is then IT $=N_L C_L=1.19 \cdot 10^5 (4.7 \cdot 10^{-2})$ $=5.5 \cdot 10^3$ mtr or, in feet, IT $=5.5 \cdot 10^3(3.28)=1.8 \cdot 10^4$ ft.

Using No. 37 AWG wire, the DC resistance of the coils is $$R_L = r_i l_T, \text{ or } R_L = 523.1 \cdot 10^{-3} \frac{\Omega}{ft}(1.8 \cdot 10^4 \text{ ft}) = 9.4 \cdot 10^3 \Omega.$$

The weight of the coil is then $w_L=w'$ $$l_T = .06 \cdot 10^{-3} \frac{lbs}{ft}(1.8 \cdot 10^4) ft \text{ or } w_L = 1.08 \text{ lbs(per } PPU).$$

We now need to determine the DC resistance of the blood, $R_b$, as is seen/presented to the electric drive by the blood within the volume $\psi_i$.

The area of each electrode in the active region is $A_b=w_b h_b$ $A_b=6 \cdot 10^{-3}(1.5 \cdot 10^{-2})=9 \cdot 10^{-5})mtr^2$. Given that the resistivity of blood, $P_b$, =1.36 Ω mtr, then the resistance $R_b$ becomes $$R_b = 1.36 \frac{d_f}{A_b} = 1.36 \frac{4.5 \cdot 10^{-3}}{9 \cdot 10^{-5}} = 68\Omega$$

with an electric drive current $i_b$=350 ma, the electric drive voltage $V_b$ becomes $V_b=i_b(68)=3.5 \cdot 10^{-1} (68)=23.8$ volts.

The magnetic drive voltage, $V_L$, is then given by $V_L=i_L R_L$, or $V_L=(2 \cdot 10^{-2}) (9.4 \cdot 10^3)=188$ volts.

Then, the power requirements are:
1. For the electric drive, $P_b=V_b i_b=23.8(3.5 \cdot 10^{-1})=8.33$ watts
2. For the magnetic drive, $P_L=V_L i_L=(2 \cdot 10^{-2})=3.76$ watts Thus, the total power requirements for the PPU is PT=12.09 watts. It is of interest to calculate the coronary/volumetric output from the heart when the flow-tube diameter $d_f$ is "increased" to 4.5 mm. Then, the new active volume $\Psi_a$ (keeping the same electrode length $h_b$=1.5 cm becomes $$\psi_a = \pi \frac{d^2 f}{4} h_b = \pi \frac{4.5 \cdot 10^{-3}(1.5 \cdot 10^{-2}) = 2.38 \cdot 10^{-7}}{4} mtr^3$$

Now, we had previously determined using Equation No. (2), that for a coronary output rate $\Psi_o^1$, the prf necessary was given by $$fr = \frac{\psi_o^1}{\psi_a} \quad (12)$$

The coronary output to the aorta (systemic output) is $$\psi_{oL}^1 = \frac{cm^3}{min} \text{ or, } \psi_{oL}^1 = 89.08 \frac{cm^3}{sec}.$$

While the output to the pulmonary arteries is $$\psi_{oR}^1 = 5,184.65 \frac{cm^3}{min} \text{ or, } \psi_{oR}^1 = 86.41 \frac{cm^3}{sec}.$$

The respective prfs are then:

$$fr_L = \frac{89.08 \text{ cm}^3}{\sec 2.38 \cdot 10^{-1} \text{ cm}^3} \text{ or, } fr_L = 374 \text{ pps and,}$$

$$fr_R = \frac{86.41 \text{ cm}^3}{\sec 2.38 \cdot 10^{-1} \text{ cm}^3} = 363 \text{ pps.}$$

We have now obtained the number of pulses arriving at the active region of each PPU, and this represents the energy deposition on the blood of mass $M_b$ which would produce a temperature rise in the blood. Since the mass $M_b$ is given as $M_b=\rho_v \Psi_a$, then with the volume density of the blood, ρv, is given by $$pv = 1.07 \cdot \frac{10^{-9} \text{ kg}}{mtr^3},$$

we have $m_b=1.07 \cdot 10^{-9}(2.38 \cdot 10^{-7})$ or, $M_b=2.54 \cdot 10^{-16}$ kg.

Now we had previously found that each electric drive pulse produces a power dissipation of $pp=V_b i_b=8.33$ watts.

Also, in accordance with Equation No. (10), we can arbitrarily choose a pulse width, $t_d$ that is greater than 3.8 ns. Hence, choosing $t_d=10^{-6}$ sec, we can say that the energy deposition by each pulse can be written as $E_p=P_P t_d$. Therefore, knowing the prfs, $f_r$, obtained previously, we can determine the total energy deposition on each PPU, as $E_a=P_P t_d f_r$, joules/sec.

Therefore, for the left PPU, Equation No. (14) gives an energy deposition of $E_{aL}=8.33(10^6 \cdot 374)=3.1 \cdot 10^{-3}$, while the right PPU receives an energy deposition of $$E_{aR} = 8.33(10^6 \cdot 363) = 3.0 \times 10^{-3} \frac{j/s}{\sec}.$$

It follows that the blood mass $M_b$ will increase its temperature T by an incremental amount ΔT in accordance with the specific heat, $C_{sp}$, of the blood, such that $E_a=M_b C_{sp} \Delta T$ (15). Now, from Equation No. (12) we can see that $E_a$ is a function of time $E_{a(t)}$ and since $M_b$ and $C_{sp}$ are constants we can take the time derivation of Equation No. (15) such that using a "prime" notation, $$T' = \frac{E_a'}{M_b C_{sp}} \quad (16)$$

For the case of human blood, the specific heat, $$C_{sp} = \frac{3.6 \cdot 10^3 \text{ } j/s}{M_b^o C}.$$

Thus, substitution of the results of Equation No. (14) gives the temperature rate of change of the blood as it passes each PPU. Thus, for the left PPU, $$T_L' = 3.1 \cdot 10^{-3} \frac{^o C}{hr}.$$

Then, for the right side, we have $$T_R' = 2.9 \cdot 10^{-3} \frac{^o C}{hr}.$$

It should be noted that these two rates of temperature increase cannot be added algebraically since they are a result of energy deposition to two different and physically isolated regions of the body. Further, with such low values for the temperature rates, the homeostatic control system of the human body should be able to easily compensate the temperature and maintain it at its normal level, allowing us to disregard such small temperature effects.

In addition to the temperature effects that were postulated by the particular use of MHD, another question arose as to the possibility that MHD might produce "hemolysis" of the red-blood cells. To address that question, we need to look at osmotic processes, since they represent the driving mechanisms that produce hemolysis. Now, osmosis is a diffusion process that requires a certain length of time interval to reach its conclusion. Therefore, we need to look at the cell-wall as permeable membrane and identify its characteristics.

It is known that the cell's membrane helps regulate the cell's volume by controlling the osmolarity of the cell. Initially, it can be assumed that within the active region of the PPU, a cell resides in a state of diffusion equilibrium where there is no net movement of extra cellular species across the cell membrane, in an isotonic environment. However, when an electric drive pulse arrives at the active region, the ions of the blood will be moved by the field and will produce a change in the species concentrations in the local regions around the electrodes. One electrode will experience a higher concentration of particles, thus creating a hypertonic region. The opposite electrode will then see a hypotonic environment. Thus, it might be postulated that our design might produce not only "hemolysis" but also "crenation". In either case, an osmotic mechanism would be governing the process. To assess the possible magnitude of those effects, let us first define the cell membrane as an electrical network containing resistance R, and capacitance C. The resistance R is related to the membrane permeability, while the capacitance component is the result of considering the cytoplasm and the extracellular fluid as two conductors separated by the non-conducting membrane to produce a capacitive value C and a resulting network with a time-constant of $\tau=RC$ sec. It has been found that $\tau$ varies from 1 to 20 ms. (see reference 4, pg. 110), for a typical membrane. Also, when a cell is excited by a singularity function such as a step waveform, the resulting response displays the usual exponential behavior of an RC electrical network.

Now, our heart design involves several time-scales encountered throughout the design as follows:
1. $\tau_t$=the transit time of a charge when the electrode potential $V_b$ is applied.
2. $\tau_d$=the dwell-time of a charge from one end of the electrode to the other end.
3. $\tau_p$=pulse-width of the pulse arriving at the active region.
4. $\tau_o$=the osmotic time-constant of the cell.

Since $\tau_o >> (\tau_p, \tau_t, \tau_d)$, then we can conclude that this heart design does not allow sufficient time for production of hemolysis or crenation. Therefore, the red blood cells are unaffected by the propulsion mechanism (MHD) used in our design, and will be able to carry out their biological functions in the blood circulation, and remain undamaged.

It is convenient at this time to list all the parameters of the heart design and present them in a single location. This is accomplished in the following Table A-1.

Magnetic flux density $B_y$=0.59 Feslab
  Systolic blood pressure used $p_b$=100 mn Hg=$1.33 \cdot 10^4$ Pascals
  Flow-tube diameter used, $d_f$=4.5 mm
  DC resistance of magnetic coils, $R_{RL}$=$9.4 \cdot 10^3$ $\Omega$
  DC resistance of blood within active volume, $R_b$=68 $\Omega$
  Electric drive current, $i_b$=350 ma ($3.5 \cdot 10^{-1}$a)
  Electric drive voltage, $V_b$=23.8 volts (=pulse amplitude)
  Electric drive power, $P_b$=8.33 watts
  Magnetic drive voltage, $V_L$=188 volts
  Magnetic drive power, $P_L$=3.76 watts Table A-1—Principle Parameter Values for the Artificial Heart Design
  Total PPU Power, $P_t$=12.09 watts (E and M)
  Pulmonary output, $CO_P$=5.2 lts/min (right PPU)
  Systemic (aorta) coronary output, $CO_A$=5.3 lts/min (left PPU)
  prf for left PPU, $fr_L$=374 pps
  prf for right PPU, $fr_L$=363 pps
  Temperature rise rate for left PPU, $T_L^1$=$3.1 \cdot 10^{-3}$° c/hr
  Temperature rise rate for right PPU, $T_R^1$=$2.9 \cdot 10^{-3}$° c/hr
  Number of turns for magnetic drive coils, NL=$1.19 \cdot 10^5$ turns
  Wire size used for magnetic active coils, No. 37 AWG annealed copper, enamel coated Having thus disclosed a preferred embodiment of the invention, it will be understood that many variations and modifications are contemplated. Accordingly, the scope hereof is to be limited only by the appended claims and their equivalents.

I claim:

1. An artificial heart comprising two fully implantable propulsion units for propelling blood through the body, each said propulsion unit including a flow tube having an axially extended chamber defining a passage for blood flow therethrough, a pair of planar electrodes disposed within said chamber, said propulsion units being operable to generate an electric field and a magnetic field in orthogonal relation to said passage;
  wherein said propulsion units include a first such unit for pulmonary circulation and a second such unit for systemic circulation, said propulsion units operating at different frequencies.

2. The artificial heart recited in claim 1 wherein each said propulsion unit is powered solely by an external power source with power being transferred transcutaneously by induction.

3. The artificial heart recited in claim 1 wherein each said propulsion unit includes a pair of inductive coils wound about axes extending transaxially away from said passage.

4. The artificial heart recited in claim 3 wherein each said inductive coil is wound about a coil core projecting transversely from said flow tube.

5. The artificial heart recited in claim 3 wherein each said inductive coil is disposed outside said flow tube.

6. An artificial heart comprising a pair of magnetohydrodynamic blood pumps for propelling blood as a working fluid through the circulation system of the body;
  each said magnetohydrodynamic blood pump including a flow tube having an axially extended chamber defining a passage for blood flow therethrough, a pair of electrodes disposed within said chamber, and a pair of inductive coils wound about axes extending transaxially away from said passage;
  a first such blood pump for pulmonary circulation and a second such blood pump for systemic circulation, said pumps operating at different frequencies.

7. The artificial heart recited in claim 6 wherein each said blood pump is powered solely by an external power source with power being transferred transcutaneously by induction.

8. The artificial heart recited in claim 6 wherein each said inductive coil is wound about a coil core projecting transversely from said flow tube.

9. The artificial heart recited in claim 8 wherein each said inductive coil is disposed outside said flow tube.

* * * * *